US00PP09554P

United States Patent [19]

Olesen et al.

[11] Patent Number: Plant 9,554

[45] Date of Patent: May 21, 1996

[54] SHRUB ROSE PLANT NAMED 'POULNINO'

[75] Inventors: Pernille Olesen; Mogens N. Olesen, both of Fredensborg, Denmark

[73] Assignee: De Vor Nurseries, Inc., Watsonville, Calif.

[21] Appl. No.: 380,103

[22] Filed: Jan. 30, 1995

[51] Int. Cl.[6] ..... A01H 5/00

[52] U.S. Cl. ..... Plt./1

[58] Field of Search ..... Plt./1, 28, 29

*Primary Examiner*—Howard J. Locker

*Attorney, Agent, or Firm*—Christie, Parker & Hale

[57] ABSTRACT

A shrub rose variety producing red flowers.

1 Drawing Sheet

SUMMARY OF THE INVENTION

The present invention relates to a new and distinct shrub rose variety which was originated by our crossing as seed and pollen parents two unnamed and undistributed seedlings of our creation. The varietal denomination of this new rose is 'Poulnino'.

Among the novel characteristics possessed by this new variety which distinguish it from its parents and all other varieties of which we are aware are its attractive red flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other useful forms of asexual reproduction may be also employed.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used as in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Ovoid.

(3) *Color.*—When sepals first divide, bud color is near 60A.

(4) *Sepals.*—Longer than bud, about 2 cm long, spread and reflex when bloom opens; some sepals are foliaceous. Color: Near 166A with tinges of near 144A at base.

(5) *Peduncle.*—Length: About 4 to about 5.5 cm. Aspect: Small prickles. Strength: Erect, sturdy. Color: Near 144A.

(6) Bracts.—At base of each cluster; 2 to 3; near 187A on edges when young, near 147A when mature, leaf-like; about 2.5 to 5 cm below calyx.

B. Bloom:

(1) *Size.*—Average size when fully expanded — about 4.5 cm to about 5.5 cm.

(2) *Borne.*—Clusters of about 5 to 11 blooms.

(3) *Form.*—Imbricated, petals ruffled at edges and roll under at maturity.

(4) *Petalage.*—Number of petals under normal conditions — about 18 to 22.

(5) *Color* (⅓ to ½ open). —Outer petals — Top Surface: between near 46A and 46B (nearer to 46B); Undersurface: near 53C. Inner Petals — Top Surface: between near 46A and 46B (nearer to 46B); Undersurface: near 53C. Base of petals — (point of attachment): Near 150D. General tonality from a distance — Velvety red.

(6) *Color (fully open).*—Outer — Top surface: between near 46A and 46B (nearer to 46B); Undersurface: near 53C. Inner petals — Top surface: near 45A; Undersurface: near 53B. Base of petals — (point of attachment): Near 150D. General tonality from a distance — Velvety red.

(7) *Color change.*—As bloom ages — Holds the velvety red color throughout. Petal top surface — Color holds constant. Petal undersurface — Color holds constant. General tonality at a distance — Velvety red.

C. Petals:

(1) *Texture.*—Thick.

(2) *Appearance.*—Inside velvety and outside somewhat satiny.

(3) *Form.*—Elliptic with slightly ruffled edges.

(4) *Arrangement.*—Imbricated.

(5) *Petaloids.*—Few.

(6) *Fragrance.*—None.

(7) *Lasting quality.*—Not suitable for cut flower.

(8) *Persistence.*—Petals drop off cleanly.

REPRODUCTIVE ORGANS

A. Stamens:

(1) *Arrangement.*—Regularly arranged around styles.

(2) *Anthers.*—Color near 19A.

(3) *Filaments.*—Near 150B.

(4) *Pollen.*—Color — near 19A.

B. Pistils:

(1) Styles.—Bunched, with even length.

(2) Stigmas.—Color near 16C at tip, balance near 33B with near 150C at base.

C. Characteristics of hips: Not observed.

PLANT

A. Form: Upright, compact.

B. Growth: Very vigorous; about 76 cm to about 92 cm in height and width at first season.

C. Foliage: Some compound 3 and 5 leaflets but mostly compound 7 leaflets.

(1) *Size.*—Small.

(2) *Quantity.*—Abundant.

(3) *Color.*—New foliage — upper side near 147A edged with near 59B; underside near 147B overlayed with near 60B; mature foliage — upper side near 147A, underside near 147B.

(4) *Shape.*—Ovate.

(5) *Texture.*—Upper side glossy, smooth; underside semi-leathery, matte.

(6) *Edge.*—Serrate.

(7) *Serration.*—Denticulate.

(8) *Leaf stem.*—Color — medium green.

(9) *Stipules.*—Long, narrow, adnate and parallel, glandular edging; pointed wing tips.

(10) *Rachis.*—Small prickles on underside

(11) *Petioles.*—Top near 146B, underside near 146D.

(12) *Auricle.*—Thin, slightly glandular.

(13) *Resistance to disease.*—Very resistant to black-spot, mildew and rust.

D. Wood:

(1) *New wood.*—Color near 144B, bark smooth.

(2) *Old wood.*—Color near 143A, bark smooth.

E. Flower stem: About 22 cm to about 36 cm from last cut.

F. Thorns:

*Quantity.*—On main stalk, average; laterals from stalk, average.

*Form.*—Thin, slightly curved downward.

*Length.*—Medium.

*Color.*—Light green.

*Position.*—Irregular.

*Prickles.*—Only on upper stem where first flower is cut.

G. Winter hardiness: Winter hardy in Denmark and in Watsonville, Calif.

We claim:

1. A new and distinct shrub rose variety, substantially as shown and described.

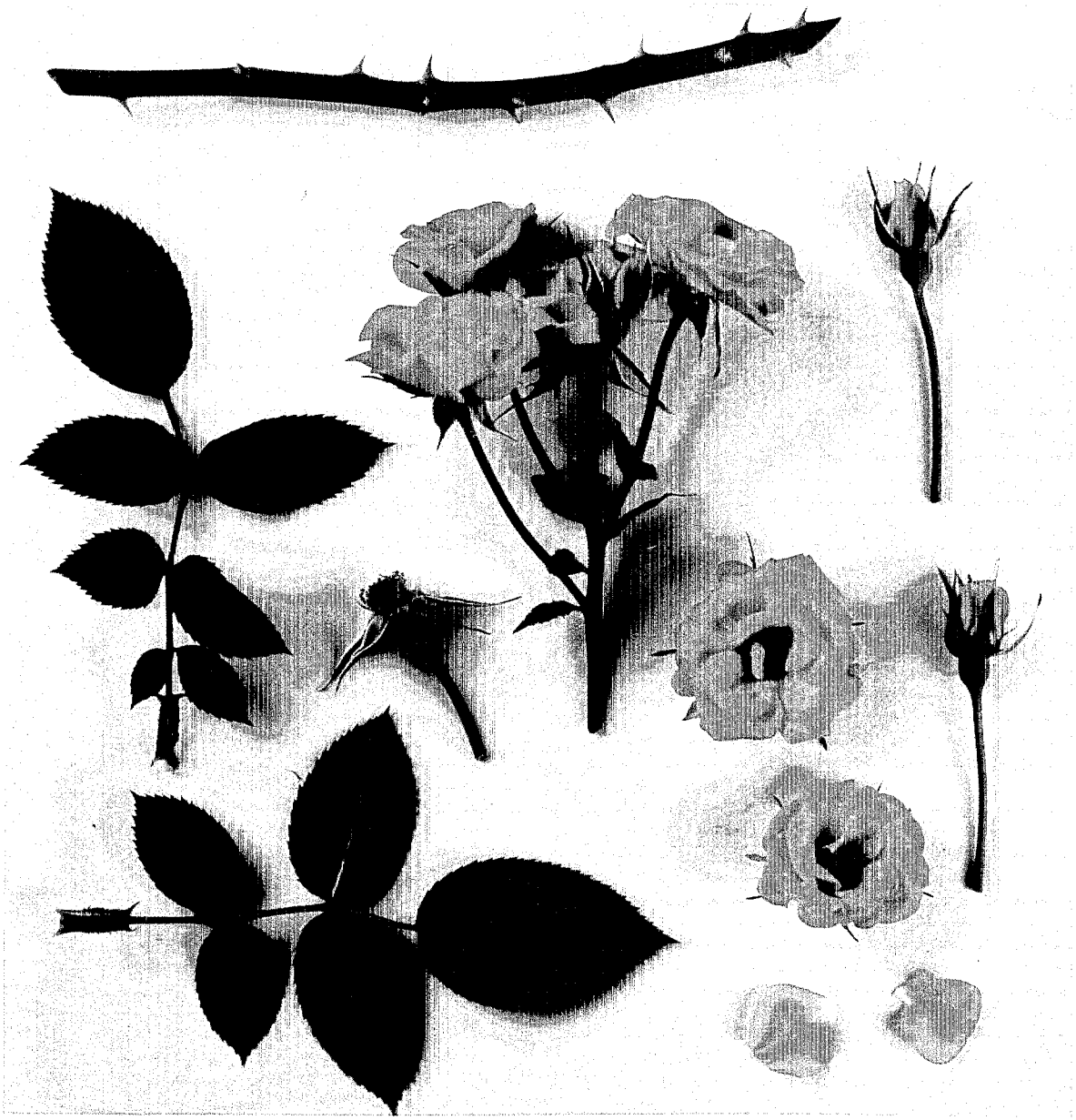

* * * * *